United States Patent
Collins et al.

(10) Patent No.: US 9,873,964 B2
(45) Date of Patent: Jan. 23, 2018

(54) DISPERSIBLE NON-WOVEN FABRICS

(71) Applicant: LENZING AG, Lenzing (AT)

(72) Inventors: Geoffrey Williams Collins, Derby (GB); Andrew Peter Slater, Warwickshire (GB); Shayda Rahbaran, Vöcklabruck (AT)

(73) Assignee: Lenzig Aktiengesellschaft, Lenzing (AT)

( * ) Notice: Subject to any disclaimer, the term of this patent is extended or adjusted under 35 U.S.C. 154(b) by 0 days.

(21) Appl. No.: 15/348,019

(22) Filed: Nov. 10, 2016

(65) Prior Publication Data

US 2017/0073863 A1    Mar. 16, 2017

Related U.S. Application Data

(62) Division of application No. 14/356,519, filed as application No. PCT/AT2012/000259 on Oct. 11, 2012.

(30) Foreign Application Priority Data

Nov. 9, 2011    (AT) ................ A 1658/2011

(51) Int. Cl.
| | | |
|---|---|---|
| *D21H 13/08* | (2006.01) | |
| *D21H 11/18* | (2006.01) | |
| *D04H 1/40* | (2012.01) | |
| *D04H 1/425* | (2012.01) | |
| *A61K 8/02* | (2006.01) | |
| *D04H 1/4258* | (2012.01) | |
| *D21H 27/00* | (2006.01) | |
| *A61K 8/73* | (2006.01) | |
| *A61Q 19/00* | (2006.01) | |
| *D04H 1/488* | (2012.01) | |
| *D04H 1/492* | (2012.01) | |

(52) U.S. Cl.
CPC ........... *D04H 1/425* (2013.01); *A61K 8/0208* (2013.01); *A61K 8/731* (2013.01); *A61Q 19/00* (2013.01); *D04H 1/40* (2013.01); *D04H 1/4258* (2013.01); *D04H 1/488* (2013.01); *D04H 1/492* (2013.01); *D21H 11/18* (2013.01); *D21H 13/08* (2013.01); *D21H 27/002* (2013.01); *A61K 2800/10* (2013.01)

(58) Field of Classification Search
CPC ...... D21H 13/08; D21H 27/002; D21H 11/18; D21H 11/20; D21H 11/12; D21H 21/18; Y10T 442/689; Y10T 428/249965; Y10T 428/2965; Y10T 428/2904; Y10T 442/3772; Y10T 442/663; Y10T 428/31986; Y10T 428/24455; D04H 1/492; D04H 1/425; D04H 1/4258; D04H 1/488; D04H 1/04; A61K 8/0208; A61K 8/731; A61Q 19/00; A61Q 19/10
See application file for complete search history.

(56) References Cited

U.S. PATENT DOCUMENTS

| | | | | |
|---|---|---|---|---|
| 3,563,241 A * | 2/1971 | Evans | ..................... | A61L 15/28 160/169 |
| 3,785,918 A * | 1/1974 | Kawai et al. | .......... | D21H 13/08 162/146 |
| 4,246,221 A * | 1/1981 | McCorsley | .............. | C08J 3/096 210/500.29 |
| 4,416,698 A * | 11/1983 | McCorsley | .............. | C08J 3/096 106/200.2 |
| 5,725,821 A * | 3/1998 | Gannon | .................... | D01F 2/00 264/203 |
| 5,746,959 A * | 5/1998 | Cox | .......................... | D01F 1/10 264/182 |
| 6,042,769 A * | 3/2000 | Gannon | .................... | D01F 2/00 264/203 |
| 6,258,210 B1* | 7/2001 | Takeuchi | .................. | B32B 5/26 162/115 |
| 6,287,419 B1* | 9/2001 | Takeuchi | ............... | D21H 13/08 162/115 |
| 6,602,386 B1* | 8/2003 | Takeuchi | ............... | D21H 13/08 162/115 |
| 6,699,806 B1* | 3/2004 | Takeuchi | ............... | D21H 13/08 442/340 |
| 6,749,718 B2* | 6/2004 | Takai | ................... | D21H 25/005 162/109 |
| 6,841,038 B2* | 1/2005 | Horenziak | ............. | D21H 13/08 162/129 |
| 7,210,205 B2* | 5/2007 | Takeuchi | ............... | D21H 13/08 28/103 |
| 7,241,711 B2* | 7/2007 | Takai | ................... | D21H 25/005 162/147 |
| 7,250,382 B2* | 7/2007 | Takai | ..................... | D21H 11/12 162/147 |
| 7,381,294 B2* | 6/2008 | Suzuki | ..................... | D21D 1/20 162/102 |

(Continued)

FOREIGN PATENT DOCUMENTS

| | | |
|---|---|---|
| DE | 19963983 A1 | 7/2001 |
| EP | 1124008 A1 | 8/2001 |

(Continued)

*Primary Examiner* — Jose Fortuna
(74) *Attorney, Agent, or Firm* — Fitzpatrick, Cella, Harper & Scinto

(57) ABSTRACT

The present invention relates to a dispersible nonwoven fabric comprising pulp and solvent spun cellulosic fibers, characterized in that the solvent spun cellulosic fibers are fibrillated. Furthermore the invention concerns the use of the fabric in dry wipes and wet wipes.

32 Claims, 1 Drawing Sheet

(56) References Cited

U.S. PATENT DOCUMENTS

| | | | | |
|---|---|---|---|---|
| 7,494,563 B2* | 2/2009 | Edwards | ............... | D21F 11/006 162/109 |
| 7,718,036 B2* | 5/2010 | Sumnicht | ............... | D21C 9/005 162/109 |
| 7,758,724 B2* | 7/2010 | Akai | ............... | B31F 1/07 156/209 |
| 7,781,104 B2* | 8/2010 | Kubo | ............... | D21H 27/00 29/623.1 |
| 7,985,321 B2* | 7/2011 | Sumnicht | ............... | D21C 9/005 162/109 |
| 8,778,086 B2* | 7/2014 | Sumnicht | ............... | D21H 13/08 134/25.2 |
| 2001/0000585 A1* | 5/2001 | Cruise | ............... | B32B 5/26 156/313 |
| 2003/0056916 A1* | 3/2003 | Horenziak | ............... | D21H 13/08 162/157.7 |
| 2003/0099821 A1* | 5/2003 | Takai | ............... | D21H 11/12 428/292.1 |
| 2003/0100240 A1* | 5/2003 | Takai | ............... | D21H 25/005 442/408 |
| 2003/0178166 A1* | 9/2003 | Takeuchi | ............... | D21H 13/08 162/146 |
| 2004/0103507 A1* | 6/2004 | Takeuchi | ............... | D21H 13/08 28/104 |
| 2004/0178142 A1* | 9/2004 | Koslow | ............... | A61L 2/0017 210/500.29 |
| 2004/0206463 A1* | 10/2004 | Luo | ............... | D01F 2/00 162/21 |
| 2004/0209078 A1* | 10/2004 | Luo | ............... | D01F 2/00 428/375 |
| 2006/0037724 A1* | 2/2006 | Akai | ............... | B31F 1/07 162/117 |
| 2008/0173418 A1* | 7/2008 | Sumnicht | ............... | C08B 1/003 162/146 |
| 2008/0173419 A1* | 7/2008 | Sumnicht | ............... | C08B 1/003 162/146 |
| 2008/0274409 A1* | 11/2008 | Harada | ............... | D21H 13/16 429/247 |
| 2009/0020139 A1* | 1/2009 | Sumnicht | ............... | D21H 13/08 134/6 |
| 2009/0020248 A1* | 1/2009 | Sumnicht | ............... | D21H 13/08 162/141 |
| 2009/0126885 A1* | 5/2009 | Akai | ............... | B31F 1/07 162/117 |
| 2009/0155556 A1 | 6/2009 | Yasumitsu et al. | | |
| 2009/0312731 A1* | 12/2009 | Steindl | ............... | A61F 13/51 604/374 |
| 2010/0272938 A1* | 10/2010 | Mitchell | ............... | D21H 13/40 428/36.1 |
| 2010/0288456 A1* | 11/2010 | Westland | ............... | D21H 17/35 162/57 |
| 2011/0265965 A1* | 11/2011 | Sumnicht | ............... | D21C 9/005 162/111 |
| 2011/0293931 A1* | 12/2011 | Vogel | ............... | A61K 8/0208 428/340 |
| 2012/0021178 A1* | 1/2012 | Miller | ............... | B31F 1/126 428/156 |
| 2012/0080155 A1* | 4/2012 | Konishi | ............... | D04H 1/4258 162/146 |
| 2012/0164514 A1* | 6/2012 | Hayakawa | ............... | H01M 2/145 429/144 |
| 2012/0180815 A1* | 7/2012 | Sumnicht | ............... | D21H 13/08 134/6 |
| 2012/0184164 A1* | 7/2012 | Gupta | ............... | D21H 13/02 442/60 |
| 2012/0285640 A1* | 11/2012 | Westland | ............... | D21H 17/35 162/57 |
| 2014/0318726 A1* | 10/2014 | Collins | ............... | A61K 8/0208 162/146 |
| 2015/0247288 A2* | 9/2015 | Collins | ............... | A61K 8/0208 162/146 |
| 2017/0016183 A1* | 1/2017 | Miller | ............... | D21H 21/18 |
| 2017/0073863 A1* | 3/2017 | Collins | ............... | A61K 8/0208 |
| 2017/0133165 A1* | 5/2017 | Ichimura | ............... | H01G 11/52 |

FOREIGN PATENT DOCUMENTS

| | | | | |
|---|---|---|---|---|
| EP | 2441869 A1 | * | 4/2012 | ........... D04H 1/4258 |
| GB | 2384249 A | * | 7/2003 | ............... D06B 3/28 |
| JP | 2006291437 A | * | 10/2006 | |
| JP | 4976675 B2 | * | 7/2012 | |
| WO | 200224990 A1 | | 3/2002 | |
| WO | WO 2007124522 A1 | * | 11/2007 | ............. A61F 13/51 |
| WO | WO 2010143736 A1 | * | 12/2010 | ........... D04H 1/4258 |
| WO | WO 2013067557 A1 | * | 5/2013 | ........... A61K 8/0208 |

* cited by examiner

DISPERSIBLE NON-WOVEN FABRICS

The present application is a division of U.S. patent application Ser. No. 14/356,519, filed May 6, 2014, which is a national stage filing under 35 U.S.C. § 371 of International Patent Application No. PCT/AT2012/000259, filed Oct. 11, 2012, which claims priority to Austrian Patent Application No. A 1658/2011 filed Nov. 9, 2011, the entire disclosure of each of which is incorporated by reference herein.

BACKGROUND OF THE INVENTION

Field of the Invention

This invention is directed towards rapidly dispersible absorbent nonwoven fabrics and methods for making and using such products. This invention is especially directed towards rapidly dispersible wet wipes that are flushable through a standard toilet system and disintegrate into easily dispersible fragments that biodegrade after disposal.

Not-woven textiles are defined with the terminology "nonwoven". The definition of nonwoven is described in the norm ISO 9092:1988. Absorbent nonwoven fabrics include materials such as dry wipes, wet wipes and cosmetic wipes and masks. They are also materials used in hygiene products like panty liners, sanitary napkins and incontinence products. The nonwoven fabrics used in these applications should fulfil the requirements of European Pharmacopoeia.

Disposable absorbent wipes such as toilet wet wipes offer high levels of convenience, comfort and efficacy that are greatly appreciated by consumers. However, the popularity of these products has created a need regarding their disposal. General disposal methods used for waste materials such bin disposal for subsequent incineration or landfill are not convenient for the consumers, especially for using of toilet wet wipes. One of the alternative disposal methods is flushing the wet wipes directly into a conventional toilet. Flushing the product in the toilet, dispersing it by mechanical forces and finally biodegrading the material in the sewage system is more convenient and discrete for the consumers. For this disposal method, the suitable material should maintain its structural integrity and strength for use, but also disintegrate readily when flushing into the toilet without causing any blockage in the pumping and drain systems.

Such products like toilet wipes are pre-moistened wipes. Therefore the nonwoven fabrics used for these applications should maintain their mechanical strength and integrity in the wet state during storage and also be biodegradable in the sewage system.

Flushable wet wipes are known for example from U.S. Pat. No. 5,629,081 and EP 1 285 985 A1.

SUMMARY OF THE INVENTION

The object of the invention is to provide a dispersible nonwoven fabric with good tensile strength but which disintegrate readily when flushed.

By the present invention there is provided a dispersible nonwoven fabric comprising pulp and solvent spun cellulosic fibers characterized in that the solvent spun cellulosic fibers are fibrillated.

DETAILED DESCRIPTION OF THE INVENTION

Figure 1:
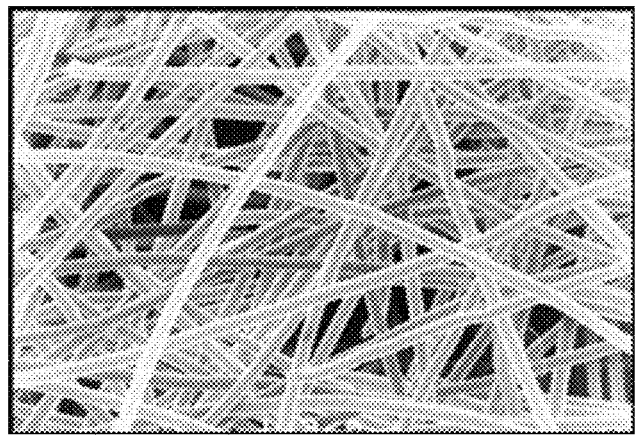
FIG. 1 shows an unfibrillated Tencel by light microscope.

Especially suited as starting material for the fibrillated fibers are solvent spun short cut cellulosic fibers with a length of 2 to 20 mm, preferably 3 to 12 mm, most preferably 4 to 10 mm. The titer of the solvent spun short cut fibers is 0.9 to 6.7 dtex, preferably 1.3 to 1.7 dtex.

Preferably the solvent spun short cut fibers are present in the dispersible nonwoven fabric in an amount of 1 to 90 wt.-%, preferably 5 to 40 wt.-%, most preferably 10 to 30 wt.-% based on the fabric.

A preferred solvent spun short cut fiber is a lyocell fiber, produced according to the Aminoxide-process, which is known e.g. from U.S. Pat. No. 4,246,221 (McCorsley). A suited solvent spun fiber is sold under the trade name "Tencel".

The dispersible nonwoven fabric has a weight of 30 to 100 g/m2, preferred of 40 to 60 g/m2 and a thickness of 0.1 to 0.7 mm.

The dispersible nonwoven fabric may comprise a dispersing aid in an amount of 0.1 to 1% wt.-%, preferably 0.5 to 1 wt.-% based on the fabric.

To increase the strength, optionally a binder is present in an amount of 0.01 to 5 wt.-%, preferably 0.1 to 0.5 wt.-% based on the fabric, preferably in form of an acrylic resin or epichlorohydrin based resin, such as polyamide-polyamine-epichlorohydrin resins or polyamide-epichlorohydrin resins. Other examples for suited binders are polyethylenimine resins and aminoplast resins.

Any type of pulps are suited, especially softwood pulps, hardwood pulps or a pulp made from plants like abaca or bamboo.

The dispersible nonwoven fabric according to the invention has a wet tensile strength in machine direction of 2 to 20 N/5 cm, preferably 3 to 13 N/5 cm and most preferably 3 to 7 N/5 cm based on a basis weight of 60 g/m2 and in cross direction 1 to 10 N/5 cm, preferably 1 to 7 N/5 cm and most preferably 1 to 3 N/5 cm. The wet tensile strength has been measured according to the EDANA Method WSP 110.4 (09) "Standard Test Method for Breaking Force and Elongation of Nonwoven Materials (Strip Method)".

One standardized test method for testing the properties of disposable wipes is known from "EDANA Guidance Document for Assessing the Flushability of Nonwoven Consumer Products". This test is used to assess the dispersibility or physical breakup of a flushable product during its transport through household and municipal conveyance systems (e.g., sewer pipe, pumps and lift stations). This test assesses the rate and extent of disintegration of a test material by turbulent water in a rotating tube. Results from this test are used to evaluate the compatibility of test materials with household and municipal wastewater conveyance systems. The principle of the test method is that the rotation of the tube is used to simulate the physical forces acting to disintegrate a product during passage through household sewage pumps and municipal conveyance systems. In this test the product is placed in a clear plastic tube containing 700 ml of tap water or raw wastewater, which is rotated end-over-end. After a specified number of cycles or rotations, the contents in the tube are passed through a series of screens. The various size fractions retained on the screens are weighed, and the rate and extent of disintegration determined.

The test material is disintegrating when at least 95% of the size fractions pass a 12 mm screen and the residue is less than 5%.

The invention also concerns a process for the production of a dispersible nonwoven fabric.

According to this wet lay process, pulp is dispersed in water and a solvent spun fiber is dispersed in water, either separately or together as a mixture. A dispersing aid such as CMC (Carboxymethyl cellulose) may be added to improve dispersion quality. The dispersions are passed through a refiner either separately or are co-refined. The refining energy is from 20 to 400 kWh/t, prefer 40 to 150 kWh/t. A binder solution may be added to the slurry. In the case of separate refining, the slurries are mixed to form an intimate blend to form one slurry. The slurry is then wet-laid, e.g. on a papermaking machine, to form a sheet. The sheet then passes through a hydroentanglement process either on-line or as a separate off-line process to form a fabric.

Figure 2:
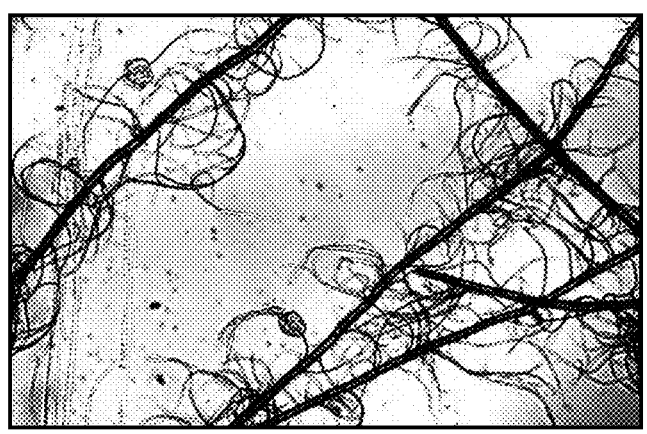
FIG. 2: shows an exemplary fibrillated Tencel by light microscope.
Figure 3:
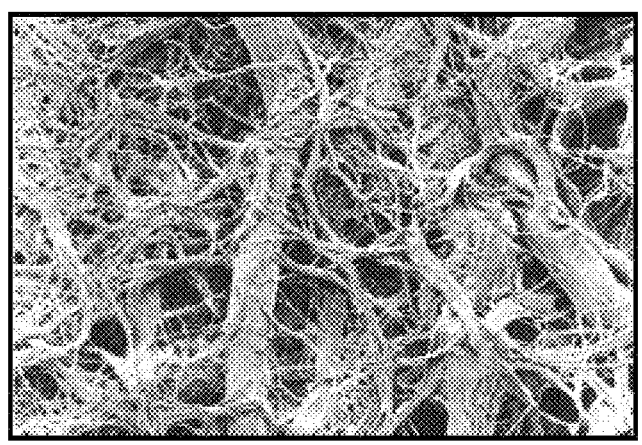
FIG. 3: shows an exemplary fibrillated Tencel by scanning electron microscope.

FIG. 1 shows an unfibrillated Tencel (light microscope). Fibrillation or refining is a wet abrasion process that exposes and releases fibrils emerging from the surface region of the filaments. As refining progresses, more fibrils are released from the filaments and the diameter of the residual filaments decreases (FIG. 2: light microscope, FIG. 3: scanning electron microscope).

In further steps the fabric is sliced into the appropriate format, folded and packed.

A treatment, preferably an impregnation, with a liquid or lotion can be carried out before packaging.

The invention is shown by the following examples:

Example 1 and Example 2 (Both Comparative)

Wetlaid fabrics made of blends of woodpulp (Camfor pulp, a long fiber woodpulp derived from spruce and pine, grown in British Columbia, Canada) with 15% Tencel short cut 1.7 dtex at 6 mm cut length (example 1) or 25% Tencel short cut 1.7 dtex at 6 mm cut length (example 2) without any refining process and without additional of any additives showed a very good dispersibility according to the Tier 1 Test-FG 511.2-Dispersability Tipping Tube Test of the "EDANA Guidance Document for Assessing the Flushability of Nonwoven Consumer Products". According to example 1, 100% of the disintegrated size fractions pass the 12 mm, the 6 mm and even the 3 mm screen, 21% retain and 79% passes the 1.5 mm screen. But the fabrics did not show a high mechanical strength, both in machine direction (MD) and cross direction (CD) as shown in Table 1.

TABLE 1

| Ex | Fiber blends | Fabric weight [g/m²] | Thickness dry [mm] | Tensile Strength wet [N/5 cm] MD | Tensile Strength wet [N/5 cm] CD | Elongation wet [%] MD | Elongation wet [%] CD | Dispersibility of samples Mass of each fraction in % in relation to dry mass >12 mm | >6 mm | >3 mm | >1.5 mm | <1.5 mm |
|---|---|---|---|---|---|---|---|---|---|---|---|---|
| 1 | 15% Tencel 85% camfor pulp | 60 | 0.65 | 2.0 | 0.9 | 2.2 | 8 | 0 | 0 | 0 | 21 | 79 |
| 2 | 25% Tencel 75% camfor pulp | 57 | 0.60 | 1.9 | 1.2 | 2.4 | 5 | 0 | 0 | 0 | 28 | 72 |

Example 3, 4 and 5

Blends of woodpulp (Camfor pulp) with 25% Tencel short cut 1.7 dtex at 6 mm cut length including an addition of 0.5% CMC dispersing aid to the slurry. In these trials the pulp/Tencel blend was refined through 1× disc refiner and 4× conical refiners in series to levels of 40 kWh/t and 60 kWh/t. Acrylic dry strength resin was added to the slurry at 1% (based on dry fiber weight). The fabrics were dispersible and the tensile strength of fabrics was improved (Table 2).

Example 6

A blend of 80% woodpulp (Camfor pulp) with 20% Tencel short cut 1.7 dtex at 6 mm cut length was used to make wetlaid fabrics. Fibers were refined to 100 kWh/t, 1% CMC (based on dry fiber weight) as dispersing aid was added and also 0.5% epichlorhydrin based wet strength resin (based on dry fiber weight) was added to increase the wet strength (Table 2). The fabric was dispersible.

TABLE 2

| Ex | Fiber blends | Refining Energy (kWh/t) | Fabric weight [g/m²] | Thickness dry [mm] | Tensile Strength wet [N/5 cm] | | Elongation wet [%] | | Dispersibility of samples Mass of each fraction in % in relation to dry mass | | | | |
|---|---|---|---|---|---|---|---|---|---|---|---|---|---|
| | | | | | MD | CD | MD | CD | >12 mm | >6 mm | >3 mm | >1.5 mm | <1.5 mm |
| 3 | 25% Tencel 75% camfor pulp | 40 | 59 | 0.28 | 3.6 | 1.3 | 4.2 | 39 | 0 | 0 | 0 | 55 | 45 |
| 4 | 25% Tencel 75% camfor pulp | 60 | 56 | 0.25 | 3.3 | 1.5 | 5.0 | 33 | 0 | 0 | 0 | 53 | 47 |
| 5 | 25% Tencel 75% camfor pulp + acrylic resin at 1% | 60 | 60 | 0.32 | 3.4 | 1.5 | 1.3 | 6.6 | 0 | 0 | 0 | 78 | 22 |
| 6 | 20% Tencel 80% camfor pulp + 0.5% epichlorohydrin | 100 | 57 | 0.23 | 5.4 | 2.1 | 2.8 | 17 | 0 | 11 | 34 | 29 | 26 |

Example 7, 8, 9 and 10

A blend of 75% woodpulp (Camfor) with 25% Tencel short cut 1.7 dtex at 6 mm cut length was used to make wetlaid fabrics. Fibers were refined to 80 kWh/t, 1% CMC as dispersing aid was added and also an epichlorhydrin based wet strength resin was added to increase the wet strength at concentrations of 0.05%, 0.10%, 0.15% and 0.20%. The results, demonstrated in Table 3, show that all samples were dispersible.

The fabric according to the invention can be used in dry wipes and wet wipes like toilette wipes, facial wipes, cosmetic wipes, baby wipes and sanitary wipes for cleaning and densification as well as in absorbent hygiene products such as panty liners, sanitary napkins and incontinence pads.

TABLE 3

| Ex | Fiber blends | Refining Energy (kWh/t) | Fabric weight [g/m²] | Thickness dry [mm] | Tensile Strength wet [N/5 cm] | | Elongation wet [%] | | Dispersibility of samples Mass of each fraction in % in relation to dry mass | | | | |
|---|---|---|---|---|---|---|---|---|---|---|---|---|---|
| | | | | | MD | CD | MD | CD | >12 mm | >6 mm | >3 mm | >1.5 mm | <1.5 mm |
| 7 | 25% Tencel 75% camfor pulp + 0.05% epichlorohydrin resin | 80 | 58 | 0.59 | 3.7 | 1.6 | 11 | 50 | 0 | 0 | 1 | 64 | 35 |
| 8 | As Ex. 7 except with 0.10% epichlorohydrin resin | 80 | 60 | 0.53 | 4.1 | 1.9 | 11 | 50 | 0 | 0 | 4 | 63 | 33 |
| 9 | As Ex. 7 | 80 | 59 | 0.29 | 6.5 | 2.6 | 2.9 | 10 | 0 | 27 | 31 | 16 | 26 |

TABLE 3-continued

| Ex | Fiber blends | Refining Energy (kWh/t) | Fabric weight [g/m²] | Thickness dry [mm] | Tensile Strength wet [N/5 cm] MD | Tensile Strength wet [N/5 cm] CD | Elongation wet [%] MD | Elongation wet [%] CD | Dispersibility >12 mm | Dispersibility >6 mm | Dispersibility >3 mm | Dispersibility >1.5 mm | Dispersibility <1.5 mm |
|---|---|---|---|---|---|---|---|---|---|---|---|---|---|
| | except with 0.15% epichlorohydrin resin | | | | | | | | | | | | |
| 10 | As Ex. 7 except with 0.20% epichlorohydrin resin | 80 | 59 | 0.42 | 5.5 | 2.2 | 8.8 | 28 | 0 | 2 | 30 | 36 | 32 |

The invention claimed is:

1. A dispersible nonwoven fabric comprising pulp and solvent spun cellulosic fibers, wherein the solvent spun cellulosic fibers are fibrillated lyocell fibers and wherein the solvent spun fibers are present in the amount of 10 to 30% wt % based on the fabric and wherein the dispersible nonwoven fabric has a wet elongation in machine direction of about 1.3% to about 11%.

2. The dispersible nonwoven fabric according to claim 1, wherein the fabric has a weight of 30 to 100 g/m², and a thickness of 0.1 to 0.7 mm.

3. The dispersible nonwoven fabric according to claim 2, wherein the fabric has a weight of 40 to 60 g/m².

4. The dispersible nonwoven fabric according to claim 1, wherein the fabric comprises a dispersing aid in an amount of 0.1 to 1 wt.-% based on the fabric.

5. The dispersible nonwoven fabric according to claim 4, wherein the dispersing aid is in an amount of 0.5 to 1 wt.-% based on the fabric.

6. The dispersible nonwoven fabric according to claim 1, wherein the fabric comprises a binder in an amount of 0.01 to 5 wt.-% based on the fabric.

7. The dispersible nonwoven fabric according to claim 6, wherein an acrylic resin or epichlorhydrin based wet strength resin is used as the binder.

8. The dispersible nonwoven fabric according to claim 6, wherein the binder is in an amount of 0.1 to 0.5 wt.-% based on the fabric.

9. The dispersible nonwoven fabric according to claim 1, wherein the pulp is selected from the group consisting of a softwood pulp, a hardwood pulp and a pulp made from plants.

10. The dispersible nonwoven fabric according to claim 9, wherein the pulp made from plants is selected from the group consisting of abaca and bamboo.

11. The dispersible nonwoven fabric according to claim 1, wherein the fabric is impregnated with a liquid or a lotion.

12. The dispersible nonwoven fabric according to claim 1, wherein the impregnated fabric has a wet tensile strength in machine direction of 2 to 20 N/5 cm, based on a basis weight of 60 g/m² and in cross direction 1 to 10 N/5 cm.

13. The dispersible nonwoven fabric according to claim 12, wherein the impregnated fabric has a wet tensile strength in machine direction of 3 to 13 N/5 cm based on a basis weight of 60 g/m² and in cross direction 1 to 7 N/5 cm.

14. The dispersible nonwoven fabric according to claim 13, wherein the impregnated fabric has a wet tensile strength in machine direction of 3 to 7 N/5 cm based on a basis weight of 60 g/m² and in cross direction 1 to 3 N/5 cm.

15. The dispersible nonwoven fabric according to claim 1, wherein the fabric is disintegrating under agitation in water according to Tier 1 Test FG 511.2-Dispersability Tipping Tube Test of the "EDANA Guidance Document for Assessing the Flushability of Nonwoven Consumer Products" where at least 95% of the disintegrated size fractions pass a 12 mm screen.

16. A product comprising the fabric according to claim 1.

17. The product according to claim 16, wherein the product is for cleaning and densification.

18. The product according to claim 17, wherein the product is selected from the group consisting of dry wipes, wet wipes and hygiene products.

19. The product according to claim 18, wherein the wipes are selected from the group consisting of toilette wipes, facial wipes, cosmetic wipes, baby wipes and sanitary wipes.

20. The product according to claim 19, wherein the hygiene products are selected from the group consisting of panty liners, sanitary napkins and incontinence pads.

21. A dispersible nonwoven fabric comprising fibrillated solvent spun cellulosic fibers, wherein the solvent spun fibers are lyocell fibers, wherein the fibrillated solvent spun cellulosic fibers are present in an amount of 10 to 30 wt.-% based on the fabric, wherein the dispersible nonwoven fabric has a wet elongation in machine direction of about 1.3% to about 11% and wherein the dispersible nonwoven fabric is obtained by a process which comprises the steps of:
  a) Providing a dispersion of pulp and a dispersion of solvent spun cellulosic fiber in water either separately or together as a mixture,
  b1) Refining these dispersions separately and mixing the resulting slurries to an intimate blend to form a slurry, or,
  b2) Co-refining the mixture of pulp and solvent spun fiber to form a slurry
  c) Wet laying the slurry to form a sheet, and
  d) Hydroentanglement of the sheet to form a fabric wherein the refining or co-refining energy is from 40 to 150 kWh/t, and wherein the solvent spun cellulosic fibers are short cut fibers with a cut length of 4 to 10 mm and a titer of 0.9 to 6.7 dtex.

22. The dispersible nonwoven fabric according to claim 21, wherein a binder is added in step b1) or b2).

23. The dispersible nonwoven fabric according to claim 21, wherein a dispersing agent is added to the dispersion in step a).

24. The dispersible nonwoven fabric according to claim 23, wherein the fabric has a wet tensile strength in machine direction of 2 to 20 N/5 cm based on a basis weight of 60 g/m$^2$ and in cross direction 1 to 10 N/5 cm.

25. The dispersible nonwoven fabric according to claim 24, wherein the fabric has a wet tensile strength in machine direction of 3 to 13 N/5 cm based on a basis weight of 60 g/m$^2$ and in cross direction 1 to 7 N/5 cm.

26. The dispersible nonwoven fabric according to claim 25, wherein the fabric has a wet tensile strength in machine direction of 3 to 7 N/5 cm based on a basis weight of 60 g/m$^2$ and in cross direction 1 to 3 N/5 cm.

27. The dispersible nonwoven fabric according to claim 21, wherein the solvent spun fibers are short cut fibers with a cut length of 2 to 20 mm and a titer of 0.9 to 6.7 dtex.

28. The dispersible nonwoven fabric according to claim 27, wherein the solvent spun fibers are short cut fibers with a cut length of 3 to 12 mm and a titer of 0.9 to 1.3 to 1.7 dtex.

29. The dispersible nonwoven fabric according to claim 28, wherein the solvent spun fibers are short cut fibers with a cut length of 4 to 10 mm.

30. The dispersible nonwoven fabric according to claim 21, wherein the fabric disintegrates under agitation in water according to Tier 1 Text FG 511.2-Dispersability Tipping Tube Test of the "EDANA Guidance Document for Assessing the Flushability of Nonwoven Consumer Products" where at least 95% of the disintegrated size fractions pass a 12 mm screen.

31. The dispersible nonwoven fabric according to claim 21, wherein the fabric has a weight of 30 to 100 g/m2 and a thickness of 0.1 to 0.7 mm.

32. The dispersible nonwoven fabric according to claim 31, wherein the fabric has a weight of 40 to 60 g/m$^2$.

* * * * *

UNITED STATES PATENT AND TRADEMARK OFFICE
CERTIFICATE OF CORRECTION

PATENT NO.        : 9,873,964 B2
APPLICATION NO.   : 15/348019
DATED             : January 23, 2018
INVENTOR(S)       : Geoffrey Williams Collins, Andrew Peter Slater and Shayda Rahbaran It is certified that error appears in the above-identified patent and that said Letters Patent is hereby corrected as shown below:

In the Specification

Column 1:
Line 34, "such" should read --such as--.
Line 59, "disintegrate" should read --disintegrates--.

Column 2:
Line 25, "g/m2" should read --$g/m^2$--.
Line 28, "1% wt.%" should read --1 wt.%--.

Column 3:
Line 14, "prefer" should read --preferably--.

Column 4:
Line 4, "additional" should read --addition--.

In the Claims

Column 7:
Line 27, "10 to 30%" should read --10 to 30--.
Line 38, "0.1 to 1%" should read --0.1 to 1--.

Column 8:
Line 63, "slurry" should read --slurry,--.
Line 65, "fabric" should read --fabric,--.

Signed and Sealed this
Fifteenth Day of May, 2018

Andrei Iancu
*Director of the United States Patent and Trademark Office*